ced Patent Number: 5,100,796
United States Patent [19]
Paridans et al.

[11] Patent Number: 5,100,796
[45] Date of Patent: Mar. 31, 1992

[54] METHODS FOR PRODUCING A NEW PSEUDOMONAS LIPASE AND PROTEASE AND DETERGENT WASHING COMPOSITIONS CONTAINING SAME

[75] Inventors: Line Paridans, Ecaussines; Lea Tirtiaux-Nafpliotis, Bierges, both of Belgium

[73] Assignee: Synfina-Oleofina, Belgium

[21] Appl. No.: 314,137

[22] Filed: Feb. 23, 1989

[30] Foreign Application Priority Data

Feb. 22, 1988 [BE] Belgium ................................ 8800207

[51] Int. Cl.$^5$ .............................................. C12N 9/20
[52] U.S. Cl. ................... 435/198; 252/174.12; 252/DIG. 12; 435/874
[58] Field of Search ............... 252/174.12, DIG. 13; 435/198, 874

[56] References Cited

U.S. PATENT DOCUMENTS 4,707,291 11/1987 Thom et al. ............... 252/174.12
4,824,599  4/1989 de Jong et al. ............ 252/174.12

FOREIGN PATENT DOCUMENTS 0218272 8/1986 European Pat. Off. .
0214761 3/1987 European Pat. Off. .
0271153 6/1988 European Pat. Off. ....... 252/174.12
0271155 6/1988 European Pat. Off. ....... 252/174.12
0271156 6/1988 European Pat. Off. ....... 252/174.12
3039579 2/1988 Japan ............................ 435/874

OTHER PUBLICATIONS

Chemical Abstracts, vol. 109, No. 4, 25 Jul. 1988, p. 81.
Chemical Abstracts, vol. 101, No. 25, 17 Dec. 1984, p. 320.

*Primary Examiner*—Lester L. Lee
*Assistant Examiner*—E. J. Kraus
*Attorney, Agent, or Firm*—Roger W. Parkhurst; M. Norwood Cheairs; John K. Abokhair

[57] ABSTRACT

A new lipase and a new protease, which can be produced by a new Pseudomonas strain, and methods of producing such lipase and protease using said strain, protease, or producing enzymatic additives for detergents whose main active component is the lipase of the invention. Further disclosed are detergent washing compositions containing the lipase and/or the protease or the enzymatic additives, and a washing process using said compositions.

5 Claims, No Drawings

METHODS FOR PRODUCING A NEW PSEUDOMONAS LIPASE AND PROTEASE AND DETERGENT WASHING COMPOSITIONS CONTAINING SAME

BACKGROUND

This invention relates to a new lipase having excellent heat resistance properties and great stability over a large pH range, as well as increased stability with regard to various denaturing agents.

Lipases are a class of enzymes which have been much studied in recent years with regard to their usefulness in numerous applications, among others, in oleochemistry or in the composition of soaps and detergents.

A large number of enzymes known to belong to the lipase class are not sufficiently effective in detergents due to the low stability of these enzymes in denaturing media. This has led to research and development of enzymes which are more stable in detergent solution.

BRIEF SUMMARY OF THE INVENTION

The new lipase of this invention can be isolated from lipolytic microorganisms, in particular from a Pseudomonas strain described hereinafter, and has particular physical and chemical properties.

The lipase of the present invention is characterized by its physical and chemical properties, comprising:
a molecular weight of approximately 55,000 daltons,
an isoelectric point of less than 4,
the capacity to hydrolyse and synthesize glycerides and esters,
activity which is non-specific with regard to the nature of the fatty acid,
maximum activity between pH 6 and pH 8, at least 50% of this being exhibited between pH 5.5 and pH 10,
stability at 30° C. for at least 30 minutes from pH 3 to pH 11.5 and for at least 150 minutes from pH 4.5 to pH 10.5,
activity at 30° C. greater than 30% of the maximum activity observed at a higher temperature,
heat stability characterized by preservation of activity of more than 75% at 60° C. for 30 minutes,
activity in detergent solution virtually equal to that exhibited in water under the same conditions, and
the capacity to remove stains in detergent solution, even in the presence of oxidizing additives,
these properties being determined as explained hereinafter.

Although it is the lipase produced by the Pseudomonas strain described hereinafter that is described here, the invention can of course also relate to any lipase having the properties mentioned hereinbefore, including the lipase produced with the aid of a microorganism strain genetically manipulated for this purpose.

DETAILED DESCRIPTION

A Pseudomonas strain producing the lipase of the invention was obtained by controlled selection of uncultivated microorganisms taken from warm waste water containing mainly fats as a substrate for those microorganisms. This strain does not belong to the known pathogenic varieties of Pseudomonas.

This strain was deposited at the Institut voor Schimmelcultures in Baarn, The Netherlands on Feb. 8, 1988 under the number CBS 134.88.

The culture conditions of this microorganism which produces the lipase of the invention are not critical because lipase production is constitutive, i.e. the microorganism produces it even in the absence of a fatty substrate. These culture conditions can therefore be adapted to produce the maximum quantity of enzyme.

Also used are culture conditions comprising a minimum medium (50 mM phosphate buffer, 0.1 g/l magnesium sulphate, 0.5 q/l trisodium citrate), and a non-fatty substrate from one of the following two categories:
either a saccharide (glucose, fructose, saccharose; 10 g/l) to which is added $NH_4+$ (ammonium sulphate, 1 g/l) to product the lipase;
or a complex substrate (15 g/l peptone, 15 g/l yeast extract or 30 g/l molasses) to produce the lipase and a protease which is completely compatible with this lipase.

The culture conditions generally comprise a pH of between 5 and 10, preferably from 6 to 7, a temperature between 15 and 40° C., preferably approximately 37° C., and adequate aeration.

The lipase is produced during the growth of the microorganism and is excreted directly into the medium. The lipase is recovered using normal techniques, generally comprising centrifuging to remove the microorganism, then concentration by ultrafiltration, followed by desalting. The crude lipase obtained in this way can then be dried. An additional purification stage is also possible in order to separate contaminating proteins from the lipase, including the protease once it has been produced, as, if the culture medium contains peptides, the strain also excretes a protease which is then found in the crude lipase.

Although the lipase can in general be produced equally well by cultivating the Pseudomonas strain in batches or continuously, it is sometimes noted that the lipolytic activity, measured in the culture medium, passes through a maximum (e.g. using, glucose or molasses as a substrate). In this case, it is preferable to use a continuous fermenter.

Finally, it is also possible to cultivate the Pseudomonas strain in the absence of oxygen, provided that a nitrate is used as a terminal electron acceptor.

The lipase of the invention exhibits hydrolytic and synthetic activity not only with regard to glycerides, but also with regard to other esters. This activity is not specific with regard to the nature of the fatty acid.

The activity of the lipase of the present invention was determined using the following methods:

a) Colorimetric analysis 0.5 ml reactive medium (100 mM sodium phosphate buffer of pH 8, containing 2.3 mg/ml sodium deoxycholate and 1.1 mg/ml gum arabic) and 0.4 ml of the sample to be measured are introduced into a micro-centrifuging tube and are incubated at the desired temperature (45° C. unless otherwise stated). The enzymic reaction is initiated by adding 0.1 ml of a freshly prepared solution of substrate (3 mg/ml p-nitrophenylpalmitate in isopropanol) and homogenization is effected immediately. After incubation (in principle 20 minutes, or less if the yellow coloring appears rapidly), the enzymic reaction is stopped by adding 0.5 ml of 3 N HCl. After centrifuging (generally 15 minutes at 13,000 rpm), 1 ml of the supernatant is removed and is mixed with 3 ml 2 N NaOH. The reflection density (which must be between 0.1 and 0.8) is read extemporaneously at 400 nm, using a standard. The value of the lipolytic activity is obtained from a standardization line. It is expressed in enzyme units (E.U) corresponding to 1 micromole of p-nitrophenol (and thus to 1 micromole of fatty acid) liberated per hour under test conditions.

Colorimetric analysis is sensitive (at least 0.1 E.U), reliable and quick. It has the advantage of being effected in an aqueous medium thus closer to the conditions of use of detergent compositions.

b) Titrimetric analysis 6 ml soya oil and 4 ml of the sample to be measured are mixed in the presence of 10 mM magnesium chloride, and the mixture is incubated at the desired temperature for 60 minutes, with vigorous stirring. After centrifuging (generally 5 minutes at 7,000 rpm), an aliquot part of the higher phase is removed, 20 ml of neutralized, denatured alcohol is added to this and it is titrated with stirring by a 0.03 N NaOH solution in the presence of phenolphtalein. The activity is again expressed in E.U.

Titrimetric analysis has the advantage of reflecting the activity of the lipase on its natural substrates, the glycerides. However, it only provides a relative (and in addition non-linear) value, dependent on the nature of the emulsion.

The activity of the lipase of the invention displays a maximum in the form of a plateau between pH 6 and pH 8 under the conditions of titrimetric analysis (citrate+-phosphate buffers of pH 3-6, phosphate buffer of pH 6-8, HCl-tris(hydroxymethyl)-aminomethane buffer of pH 8-10); the lipase exhibits at least 50% of its maximum activity between approximately pH 5.5 and 10.

The stability at the pH of the lipase of the invention was determined by maintaining the lipase at 30° C. for 30 or 150 minutes at the desired pH, then determining the residual lipolytic activity by means of colorimetry. The maximum activity is preserved for 30 minutes from pH 3 to pH 11.5, and for 150 minutes from pH 4.5 to pH 10.5. 80% of the maximum activity is still observed after 150 minutes at pH 12. Even in the presence of 0.1% Triton-X 100 (octylphenol polyethoxylate available from Rohm and Haas), 75% of the maximum activity is still observed after 45 minutes at pH 11.

The activity of the lipase of the invention is dependent on temperature. When using the titrimetric method (with a fatty substrate), it is observed that the maximum activity is at 60° C. and that the lipase exhibits more than 80% of this at 40° C. When using the colorimetric method (in an aqueous medium), the maximum activity is exhibited at 47° C. and the lipase preserves more than 60% of this at 40° C. In both cases, the lipase still exhibits more than 30% of the maximum activity at 30° C.

The lipase of the invention is remarkably stable at normal washing temperatures. After 30 minutes at 30°, 40° or 60° C., it exhibits 100, 95 and 75%, respectively, of the initial activity, these measurements being effected by the colorimetric method.

In detergent solution, the activity of the lipase of the invention is at a maximum for a concentration of approximately 5 g detergent base per liter. After 30 minutes at 30° C. in 5 g/l detergent solutions, the lipase still exhibits virtually all of its activity:
91% in a detergent base solution without an oxidizing agent with a pH of 9.4;
84% in a solution of a commercial detergent (domestic lye) with a pH of 10.26;
81% in a solution of another commercial detergent with a pH of 11.12;
69% in a solution of a third commercial detergent with a pH of 8.26.

The lipase of the invention is also characterized by its effectiveness in removing stains in detergent solution, even in the presence of oxidizing additives.

The molecular weight of the lipase of the invention is approximately 55,000 daltons, as determined by molecular sieving in the presence of Triton-X 100 (octylphenol polyethoxylate available from Rohm and Haas) in order to separate the aggregates without denaturing the enzyme. This molecular weight is considerably higher than that of the majority of the other lipases excreted by microorganisms.

It has been established that the isoelectric point of the lipase is lower than 4.

As was explained hereinabove, the Pseudomonas strain capable of producing the lipase of the invention is also apt to produce a protease. This protease is completely compatible with the lipase of the invention; it is also active in detergent solution. The protease of the invention is not always produced. When it is produced, it is produced at the same time as the lipase of the invention by the Pseudomonas strain described hereinabove, and it is possible to separate them using known techniques, e.g. by exclusion chromatography.

The following method was used to determine the proteolytic activity:

1 ml of substrate solution (0.5 g azocasein in 100 ml of 200 mM HCl-tris(hydroxymethyl)aminomethane buffer of pH 7) and 0.5 ml of the enzymic solution to be measured, sufficiently dilute, are introduced into a centrifuging tube. After 30 minutes of incubation at 37° C., 2 ml of a 0.1 g/ml solution of trichloroacetic acid is added, homogenization is effected carefully and then centrifuging is effected for 5 minutes at 5,000 rpm. 1 ml of the supernatant is then removed, this being added to 2 ml of 250 mM NaOH. The reflection density is read at 440 mM against a standard obtained by replacing the sample to be measured with distilled water in the test. In order to ensure the linearity of the method, the reflection densities read must be between 0.05 and 0.2. One proteolytic unit is the quantity of enzyme which causes an increase in the reflection density of 1.0 in relation to the standard, under the conditions of determination. This unit corresponds to approximately 1/4,000 of the proteolytic unit determined by the ANSON method.

Another feature of the invention relates to detergent compositions containing the lipase and/or the protease of the invention. The detergent compositions of the invention can be made in the form of powder or liquid, or in any other form. The active detergent constituent of these detergent compositions consists of a mixture of at least one anionic synthetic detergent and at least the non-ionic synthetic detergent. These types of detergents are well known to those skilled in the art. In general, the ratio by weight of anionic detergent to non-ionic detergent varies from 12:1 to 1:12, preferably from 6:1 to 1:6. The total amount of these two detergents in the composition is usually from 1 to 30% by weight, preferably 6 to 25%. These detergent compositions usually comprise at least one soap, generally representing 1 to 12% by weight. It is also possible to add other types of detergents, such as cationic or amphoteric detergents.

The detergent compositions generally comprise other normal ingredients in normal quantities, and these may be free of phosphates.

Thus, 1 to 45% by weight, preferably from 1 to 30%, of these compositions may consist of one or more organic and/or inorganic structuring agents. Typical examples of structuring agents of this type include alkaline ortho-, pyro- and tripolyphosphates, alkaline carbonates, alone or mixed with calcite, alkaline sulphates, alkaline silicates, alkaline citrates, alkaline nitrilotriacetates, carboxymethylcellulose, carboxylmethyloxysuccinates, zeolites and polyacetalcarboxylates. Moreover, from 1 to 35% by weight, preferably 20 to 30%, of these compositions may consist of an oxidizing agent or an oxidizing system comprising an oxidizing agent and an activator thereof. Sodium perborate is generally used as the oxidizing agent.

The liquid compositions generally have a water base (approximately 40% by weight). They can contain up to 30% inorganic solvents, such as ethanol or propylene glycol, and in general, 1 to 20% by weight, preferably approximately 10%, consists of at least one basic compound, such as triethanolamine.

These compositions also can contain bleaching agents, foam boosters, lather limiters, corrosion inhibitors, complexing or suspending agents, perfumes, dyes, stabilizing agents for the enzymes and/or for the oxidizing agents, or any other normal additive.

The lipase of the invention is added to the detergent composition at the rate of 0.1 to 50% by weight of composition, preferably from 0.5 to 10%, perhaps in the form of an enzymic additive the principal active constituent of which is the lipase of the invention, and which may also contain a protease, which is not necessarily that of the invention.

A third feature of the invention relates to a washing process using the detergents of the invention. A solution containing 1 to 20 g/l, preferably 3 to 7 g/l, detergent composition is generally used. According to a preferred embodiment of the invention, the pH of the washing solution is between 7 and 12, preferably between 8 and 11, the washing temperature is lower than or equal to 60° C., and the duration of washing is between 10 and 90 minutes, preferably between 25 and 45 minutes.

According to a preferred embodiment of the invention, lipase (or enzymic additive) of the invention is introduced into the detergent composition in such a quantity that the lipolytic activity in the washing solution is greater than 350 colorimetric E.U per ml (>0.5 volumetric E.U per ml); preferably greater than 700 colorimetric E.U per ml (>1 volumetric E.U per ml). Smaller quantities of lipase will have only a negligible effect on the result of the washing. Preferably, the lipase is introduced in such a quantity that the lipolytic activity is greater than 700 colorimetric E.U per ml (>1 volumetric E.U per ml); quantities of up to five times this amount of lipase do not appear to have any favorable or unfavorable effect on the result of the washing. When a protease is also introduced into the detergent composition, it is preferable for the proteolytic activity to be greater that 0.6 Anson units/l, preferably greater than 1 Anson unit per l.

This invention will now be described with reference to the following examples which ar given in order to illustrate more clearly the scope of the invention, but are in no way limiting.

EXAMPLE 1 (LP)

A growth and production medium consisting of a 50 mM potassium phosphate buffer of pH 6 containing 0.5 g/l trisodium citrate, 0.1 g/l magnesium sulphate and 15 g/l casein peptone was prepared and was sterilized at 121° C. for 20 minutes.

100 ml production medium cultured by a suspension drop containing the Pseudomonas strain (40% glycerol solution containing the strain and maintained at 80° C. was introduced into a 1000 ml phial (flask) and incubated at 37° C for 24 hours with orbital stirring at 200 rpm.

This culture served to inoculate a 6 liter fermenter, sterilized in situ at 121° C. for 1 hour, containing 4 liters of production medium. Stirring (nominal value : 400 to 1000 rpm) and aeration (nominal value : 6 l air per minute) were regulated in such a way that the pressure of the oxygen dissolved in the fermenter was at least equal to 5% of saturation, adding small quantities of an anti-foaming agent of a silicone nature in order to prevent any overflow due to foaming. It was incubated at 37° C. for 10 hours. During the first four hours, a rapid exponential growth phase was observed in the strain, at the end of which the lipolytic activity reached 122 colorimetric E.U per ml. Then a slow exponential growth phase was observed in the strain, ending after approximately 9 hours, and in the course of which considerable excretion of the lipase was observed:

after 6.5 hours, 375 colorimetric E.U per ml were measured;

after 9 hours, 740 colorimetric E.U per ml were measured;

after 10 hours, a plateau of 800 colorimetric E.U was reached.

After incubation, as the culture had reached the stationary phase, the microorganisms were separated by means of centrifuging. The supernatant was concentrated and dialysed against water by ultrafiltration on an AMICON hollow fiber apparatus, up to a final volume of 0.1 liter.

The lipolytic activity of this solution corresponded to 30,000 colorimetric E.U or 109.5 titrimetric E.U per ml. Its proteolytic activity corresponded to 0.077 Anson units per ml.

3.2 g crude enzymic extract in the form of a brown powder was obtained by means of freeze-drying.

EXAMPLE 2 (LPC)

The process according to Example 1 was repeated until a solution of 3.2 g crude enzymic extract in 100 ml water was obtained. To this solution, stirred to 0° C., was slowly added 200 ml acetone cooled to the same temperature, and then stirring was continued for 15 minutes. After centrifuging, the proteinic residue containing the lipase was collected, and then brought into a state of suspension in a minimum quantity of distilled water. After a microfiltration process to remove particles and/or cellular debris, the solution was freeze-dried and 800 mg beige powder was collected.

It was determined that this sample of powder contained 0.5 mg of proteins per mg powder (in relation to bovine albumin, using the Folin method). This powder exhibited lipolytic activity of 3,200 colorimetric E.U per mg, and proteolytic activity of 0.082 Anson units per mg.

EXAMPLE 3 (LC)

100 mg of the beige powder obtained in Example 2 was dissolved in 1 ml 50 mM phosphate buffer of pH 7. This solution was passed over an exclusion chromatography column (Sephadex G-150, diameter 26 mm, length 40 cm) and was eluted with a 50 mM phosphate buffer of pH 7.

As the lipase was excluded, as well as the majority of the other constituents forming aggregates with the lipase, it was eluted immediately after the dead volume of the column, free of protease which was eluted later and collected separately.

After freeze-drying of these two solutions, 92 mg beige powder containing the lipase and 2 mg white powder containing the protease were collected.

The powder containing the lipase exhibited 3,420 colorimetric E.U per mg, while the powder containing the protease exhibited 4.0 Anson units per mg.

EXAMPLE 4 (L)

A growth medium consisting of a 50 mM potassium phosphate buffer of pH 7, containing 0.5 g/l trisodium citrate, 0.1 g/l magnesium sulphate, 1 g/l ammonium sulphate and 15 g/l glucose was prepared and sterilized at 121° C. for 20 minutes.

100 ml growth medium cultured by a suspension drop containing the Pseudomonas strain (40% glycerol solution containing the strain and maintained at -80° C.) was introduced into a 1,000 ml phial and incubated at 37° C. for 24 hours with orbital stirring at 220 rpm.

This culture served to inoculate a 2 liter fermenter, sterilized in situ a 121° C. for 1 hour, containing 1.5 liters sterile production medium (identical to the sterile growth medium except that it contained only 0.35 g/l ammonium sulphate and 5 g/l glucose).

The incubation at 37° C. was started, with surface aeration of 5 l air per minute and stirring of approximately 500 rpm regulated in such a way that the pressure of the oxygen dissolved in the fermenter was equal to at least 1% of saturation.

After 7 hours there was a population of $3.4 \times 10^{10}$ cells per ml of medium and lipolytic activity in this medium corresponding to 60 colorimetric E.U per ml.

At this stage, the continuous process was started: a flow of 500 ml/h was introduced into the sterile production medium, an equivalent quantity of culture being removed at the same time, for a period of 72 hours.

36 liters of culture were collected in this way. The microorganisms were separated by means of centrifuging. The supernatant was collected and was concentrated and dialysed against water by ultrafiltration on an apparatus formed by two looped units with a separation threshold of 10,000 Daltons, up to a volume of 5 liters Concentration was continued on an AMICON hollow fiber apparatus up to a final volume of 1 liter.

The lipolytic activity of this solution corresponded to 2,000 colorimetric E.U per ml; it was left with no proteolytic activity.

40 g crude enzymic extract was obtained by freeze-drying.

EXAMPLE 5

The enzymic activity of the lipase of the invention in detergent solution was tested using standard EMPA fabric swatches (Eidgenossische Materialprufungs- und Versuchsanstalt, St Gallen, Switzerland) with standardized soils:

No. 104 : polyester/cotton 65/35 blend fabric stained with olive oil and carbon black No. 112 : cotton fabric stained with cocoa No. 117 : polyester/cotton 65/35 fabric blend stained with blood, milk and India ink.

A detergent base with the following composition was prepared in the following parts by weight:

14 parts anionic surfactant (n-alkylbenzene sulphonate)

4 parts non-ionic surfactant (polyethoxylated fatty alcohol)

2 parts soap 30 part sodium tripolyphosphate 10 parts sodium silicate 30 parts sodium sulphate 10 parts sodium carbonate 0.8 bleaching agent This detergent base was diluted at the rate of 4 g per liter distilled water. The pH of this mixture was 9.4.

Two solutions were prepared starting from this mixture, one (Example 5a) containing 2.5 g/l of the powder obtained in Example 1, and the other (Example 5b) containing 0.6 g/l of the powder obtained in Example 3. These solutions were brought to 30° C. and the residual lipolytic activity was measured as a function of the contact time, using the colorimetric method:

|  | Initial Value | After 10 Mins. | After 20 Mins. | After 30 Mins. |
| --- | --- | --- | --- | --- |
| Example 5a | 100% | 100% | 95% | 91% |
| Example 5b | 100% | 100% | 95% | 91% |

EXAMPLE 6

The enzymic activity of the lipase of the invention was tested using standard EMPA fabric swatches (Eidgenossische Materialprufungs- und Versuchsanstalt, St Gallen, Switzerland) with standardized soils:

No. 104 : polyester/cotton 65/35 blend fabric stained with olive oil and carbon black.

No. 112 : cotton fabric stained with cocoa

No. 117 : polyester/cotton 65/35 fabric blend stained with blood, milk and India ink.

Washing tests were carried out in cylindroconical phials placed in an orbital incubator at 37° C. Three remnants of the same fabric (9×9 cm) numbered in advance with known initial reflectance were introduced into a 500 ml phial containing 100 ml of the detergent solution to be tested, prepared at the last minute, and 5 ml of which was removed for enzymic determination at the starting point.

After orbital stirring at 200 rpm for 30 minutes, the fabrics were rinsed with 3×250 ml distilled water and dried by ironing, while the residual enzymic activities were determined in the solution after washing.

The average reflectance was calculated and compared with that of the unwashed fabric on the one hand, and on the other hand with that of a reference sample washed in parallel in a solution without enzyme. The following increases in reflectance were observed:

| Fabric No. | 104 | 112 | 117 |
| --- | --- | --- | --- |
| Lipase of Ex. 1 | +5.6 | +10.9 | +8.4 |
| Lipase of Ex. 2 | +9.3 | +12.1 | +6.0 |

EXAMPLE 7

The enzymic activity of the lipase of the invention in detergent solution containing an oxidizing agent was tested according to the process described in Example 6, adding 1 g/l sodium perborate to the washing solutions. The following increases in reflectance were observed:

| Swatch No. | 104 | 112 | 117 |
|---|---|---|---|
| Lipase of Ex. 1 | +5.4 | +27.7 | +5.7 |
| Lipase of Ex. 2 | +9.7 | +6.7 | +2.9 |

COMPARATIVE EXAMPLE

The known lipase used is sold under the name AMANO P, and is produced by the strain *Pseudomonas fluorescens* IAM 1057, described in more detail in Japanese Patent Application 53/20487-A by AMANO PHARMACEUTICAL CO. LTD.; Nagoya, Japan. In a 1 mg/l solution, this lipase has activity corresponding to 2,300 colorimetric E.U or 25 volumetric E.U.

The stability of this lipase in a 0.5 g/l lipase solution was observed according to the process of Example 5:
initial value 100%
after 10 mins 84%
after 20 mins 63%
after 30 mins 46%

The efficiency of this lipase in detergent solution was tested according to the process of Example 6. The following variations in reflectance were observed:

| Swatch No. | 104 | 112 | 117 |
|---|---|---|---|
| AMANO P | −1.8 | +2.5 | +3.0 |

In the presence of an oxidizing agent (process of Example 7), the following variations in reflectance were observed:

| Swatch No. | 104 | 112 | 117 |
|---|---|---|---|
| AMANO P | +2.4 | −4.3 | +0.1 |

EXAMPLE 8 AND COMPARATIVE EXAMPLE 8

The lipase of Example 2 and, for comparative purposes, a known lipase sold for use in detergent compositions by NOVO under the trade name Lipolase TM 30T.

0.5 g of the lipase was introduced in a standard detergent solution "ECE 77", used in an ECE color fastness test, having the following composition:
linear $C_{11.5}$ alkylbenzene sulfonate 0.29 g
ethoxylaced tallow ($C_{14}$) alcohol 0.105 g
sodium soap (80% $C_{18}$–$C_{22}$) 0.125 g
sodium triphosphate 1.59 g
sodium silicate ($SlO_2/Na_2O$ - 3.3) 0.27 g
magnesium silicate 0.07 g
carboxymothyl cellulose 0.04 g
sodium ethylenadiamine tetraacetate 0.01 g
sodium sulfate 0.765 g
sodium perborate 1.00 g
water up to 1 litre The colorimetric activity of each lipase was determined at 30° C. in said solution, and expressed as a fraction of the activity of the same lipase determined in aqueous solution under the same conditions:

| | Relative Colorimetric Activity | Lipase of Ex. 2 | Lipolase 30T |
|---|---|---|---|
| a) | in aqueous solution | 100% | 100% |
| b) | in detergent solution | | |
| | t-0 min | 100% | 10% |
| | t-10 min | 99% | 0% |
| | t-20 min | 95% | 0% |
| | t-30 min | 98% | 0% |

These experiments were reported without sodium perborate in the detergent composition; no significant difference was observed in the stability.

What is claimed is:

1. A detergent washing composition comprising
a lipase produced by the Pseudomonas strain deposited at the Centralbureau voor Schimmelcultures in Baarn, The Netherlands on Feb. 8, 1988 under the number CBS 134.88,
at least one anionic synthetic detergent, and
at least one non-anionic synthetic detergent, the total amount of the detergents comprising 1 to 30% by weight of the composition.

2. A lipase produced by the Psuedomonas strain of claim 1.

3. The detergent washing composition of claim 1 wherein said lipase is added to said detergent washing composition in an amount in the range from 0.1–50% by weight.

4. The detergent washing composition of claim 1 wherein said detergent washing composition is in the form of either a powder or liquid.

5. A detergent washing composition including a crude lipase of claim 2.

* * * * *